(12) United States Patent
Zhou et al.

(10) Patent No.: US 10,160,884 B2
(45) Date of Patent: Dec. 25, 2018

(54) METAL COMPOUND CHEMICALLY ANCHORED COLLOIDAL PARTICLES AND METHODS OF PRODUCTION AND USE THEREOF

(71) Applicant: Air Products and Chemicals, Inc., Allentown, PA (US)

(72) Inventors: Hongjun Zhou, Chandler, AZ (US); Xiaobo Shi, Chandler, AZ (US); Jo-Ann Theresa Schwartz, Chadds Ford, PA (US)

(73) Assignee: Versum Materials US, LLC, Tempe, AZ (US)

( * ) Notice: Subject to any disclaimer, the term of this patent is extended or adjusted under 35 U.S.C. 154(b) by 0 days.

(21) Appl. No.: 15/070,590

(22) Filed: Mar. 15, 2016

(65) Prior Publication Data

US 2016/0280962 A1   Sep. 29, 2016

Related U.S. Application Data

(60) Provisional application No. 62/136,706, filed on Mar. 23, 2015.

(51) Int. Cl.
   *C09G 1/02* (2006.01)
   *C07F 15/02* (2006.01)
   (Continued)

(52) U.S. Cl.
   CPC .............. *C09G 1/02* (2013.01); *C07F 15/02* (2013.01); *C09K 3/1445* (2013.01); *C09K 3/1463* (2013.01); *H01L 21/3212* (2013.01)

(58) Field of Classification Search
   None
   See application file for complete search history.

(56) References Cited

U.S. PATENT DOCUMENTS 4,478,748 A    10/1984   Barth
4,789,648 A    12/1988   Chow et al.
(Continued)

FOREIGN PATENT DOCUMENTS

CN    102516876 A    6/2012
CN    102585704 A    7/2012
(Continued)

OTHER PUBLICATIONS

Kang, Young-Jae, et al., Synthesis of Fe Metal Precipitated Colloidal Silica and Its Application to W Chemical Mechanical Polishing (CMP) Slurry, Journal of Colloid and Interface Science, 349 (2010), pp. 402-407.

(Continued)

*Primary Examiner* — Roberts P Culbert
(74) *Attorney, Agent, or Firm* — Lina Yang (57) ABSTRACT

Metal compound chemically anchored colloidal particles wherein the metal compound is in molecular form are disclosed. A facile and fast process to chemically anchor metal compounds uniformly onto colloidal particle surfaces via chemical bonding has been developed. Metal compounds are chemically anchored to the surface of colloidal particles via an organic linking agent. Uniformly distributed metal compounds remain in molecular form after the process. The metal compound chemically anchored colloidal particles can be used as solid catalyst in metal chemical-mechanical planarization process.

6 Claims, 2 Drawing Sheets

(51) Int. Cl.
  *C09K 3/14* (2006.01)
  *H01L 21/321* (2006.01)

(56) References Cited

U.S. PATENT DOCUMENTS

| | | |
|---|---|---|
| 6,454,819 B1 | 9/2002 | Yano et al. |
| 6,582,761 B1 | 6/2003 | Nishimoto et al. |
| 7,014,669 B2 | 3/2006 | Small et al. |
| 7,029,508 B2 | 4/2006 | Scott et al. |
| 7,427,305 B2 | 9/2008 | Scott et al. |
| 7,429,338 B2 * | 9/2008 | Siddiqui ............... B24B 37/044 216/88 |
| 2008/0286370 A1 * | 11/2008 | Kuebelbeck ....... A61K 49/1881 514/1.1 |
| 2009/0081927 A1 | 3/2009 | Grumbine et al. |
| 2011/0172331 A1 | 7/2011 | Suemura et al. |
| 2012/0028466 A1 | 2/2012 | McConnell et al. |
| 2013/0068995 A1 | 3/2013 | Ho et al. |
| 2014/0315386 A1 | 10/2014 | Zhou et al. |

FOREIGN PATENT DOCUMENTS

| | | |
|---|---|---|
| EP | 1104778 A2 | 6/2001 |
| JP | 2007095714 | 4/2007 |
| JP | 2007177137 A2 | 7/2007 |
| JP | 2009209025 A2 | 9/2009 |
| KR | 20080058272 | 6/2008 |
| WO | 9402560 | 2/1994 |
| WO | 0155028 | 8/2001 |
| WO | 2008057593 A1 | 5/2008 |
| WO | 2011042620 A1 | 4/2011 |

OTHER PUBLICATIONS

Xu, Ying, et al., Synthesis and Characterization of Iron Oxide-Coated Silica and Its Effect on Metal Adsorption, Journal of Colloid and Interface Science 282 (2005), pp. 11-19.

Dement'Eva, O. V., et al., "New Multifunctional Nanoparticles with Mesoporous Cores and Silver Shells", Colloid Journal, 2012, vol. 74, No. 4, pp. 440-444.

Samuel, Jorice, et al., "Surface Characterizations of Fluorescent-functionalized Silica Nanopartricles: From the Macroscale to the Nanoscale", J. Nanopart Res (2010), 12:2255-2265.

* cited by examiner

Figure 1

Figure 2

METAL COMPOUND CHEMICALLY ANCHORED COLLOIDAL PARTICLES AND METHODS OF PRODUCTION AND USE THEREOF

This Application claims the benefit of U.S. Provisional Application No. 62/136,706, filed on Mar. 23, 2015. The disclosure of this Application is hereby incorporated by reference.

BACKGROUND OF THE INVENTION

This invention relates generally to metal compound chemically anchored colloidal particles, the methods of production and use thereof.

The metal compound chemically anchored colloidal particles, more specifically, are colloidal particles having metal compounds uniformly anchored to the surfaces via chemical bonding. The metal compounds are in molecular form. The metal compound chemically anchored colloidal particles can be widely used in the industry, for example, to act as catalyst to increase the reaction rates for a range of different processes. For example, they can be used as a solid catalyst in chemical-mechanical planarization (CMP) of semiconductor wafers.

There are a large number of materials used in the manufacture of integrated circuits such as a semiconductor wafer. The materials generally fall into three categories—dielectric material, adhesion and/or barrier layers, and conductive layers. The use of the various substrates, e.g., dielectric material such as TEOS, plasma-enhanced TEOS (PETEOS), and low-k dielectric materials; barrier/adhesion layers such as tan copper, tantalum, titanium, tantalum nitride, and titanium nitride; and conductive layers such as aluminum, tungsten, and noble metals are known in the industry.

Integrated circuits are interconnected through the use of well-known multilevel interconnections. Interconnection structures normally have a first layer of metallization, an interconnection layer, a second level of metallization, and typically third and subsequent levels of metallization. Inter-level dielectric materials such as silicon dioxide and sometimes low-k materials are used to electrically isolate the different levels of metallization in a silicon substrate or well. The electrical connections between different interconnection levels are made through the use of metallized vias and in particular tungsten vias. U.S. Pat. No. 4,789,648 describes a method for preparing multiple metallized layers and metallized vias in insulator films. In a similar manner, metal contacts are used to form electrical connections between interconnection levels and devices formed in a well. The metal vias and contacts are generally filled with tungsten and generally employ an adhesion layer such as titanium nitride (TiN) and/or titanium to adhere a metal layer such as a tungsten metal layer to the dielectric material.

W (tungsten) has been a widely used material for the formation of contact, via and hole for connecting the inter-layer metal lines in IC fabrication due to its excellence in filling vias by Chemical Vapor Deposition (CVD).

In a typical process, via holes are etched through the interlevel dielectric (ILD) to interconnection lines or to a semiconductor substrate. Next, a thin adhesion layer such as titanium nitride and/or titanium is generally formed over the ILD and is directed into the etched via hole. Then, a tungsten film is blanket deposited over the adhesion layer and into the via. The deposition is continued until the via hole is filled with tungsten. Finally, the excess tungsten is removed by chemical mechanical polishing (CMP) to form contacts and vias.

In a typical CMP process, a substrate (e.g., a wafer) is placed in contact with a rotating polishing pad attached to a platen. A CMP slurry, typically an abrasive and chemically reactive mixture, is supplied to the pad during CMP processing of the substrate. During the CMP process, the pad (fixed to the platen) and substrate are rotated while a wafer carrier system or polishing head applies pressure (downward force) against the substrate. The slurry accomplishes the planarization (polishing) process by chemically and mechanically interacting with the substrate film being planarized due to the effect of the rotational movement of the pad parallel to the substrate. Polishing is continued in this manner until the desired film on the substrate is removed with the usual objective being to effectively planarize the substrate. Typically metal CMP slurries contain an abrasive material, such as silica or alumina, suspended in an oxidizing, aqueous medium.

The ratio of the removal rate of a metal (e.g., tungsten) to the removal rate of a dielectric base is called the "selectivity" for removal of the metal in relation to removal of the dielectric during CMP processing of substrates comprised of metal and dielectric material.

When CMP slurries with high selectivity for removal of metal in relation to dielectric are used, the metal layers are easily over-polished creating a depression or "dishing" effect in the metalized areas. This feature distortion is unacceptable due to lithographic and other constraints in semiconductor manufacturing.

Another feature distortion that is unsuitable for semiconductor manufacturing is called "erosion." Erosion is the topography difference between a field of dielectric and a dense array of metal vias or trenches. In CMP, the materials in the dense array may be removed or eroded at a faster rate than the surrounding field of dielectric. This causes a topography difference between the field of dielectric and the dense metal (e.g., copper or tungsten) array.

As industry standards trend toward smaller device features, there is a continuous developing need for tungsten CMP slurries that deliver superior planarization of the nanostructures of IC chips. Specifically, for 28 nm technology nodes and beyond applications, slurry products must deliver tunable removal rate and tunable selectivity between metal and dielectric, reduce the erosion and dishing while maintaining sufficient removal rate.

The slurry chemistry plays a major role in removing the W material by CMP process. The W slurry should consist of suitable abrasives with appropriate chemicals to meet the requirements. Usually an oxidizer is added to W slurry since it plays a key role in increasing the removal rate by forming the passive tungsten oxide layer, which is softer than W material, onto the surface and this surface is mechanically abraded by abrasive particles.

Colloidal silica plays a key role as a polishing slurry for CMP process. Several attempts have been done in modifying these slurries to make it suitable for the CMP process for different materials and applications.

Recently work has been performed on coating of the catalyst to the abrasive to enhance the chemical reaction between oxidizing agent and the metal to be polished during CMP process.

U.S. Pat. No. 4,478,742 discloses a method of producing iron acetate coated silica sol comprising the steps of passing a mixture of ion free colloidal silica and an inorganic iron salt in contact with a strong base anion exchange resin in the acetic acid salt form under conditions whereby the iron salt is converted to the iron acetate and is coated on the silica sol, thereby producing an iron acetate coated silica sol.

U.S. Pat. Nos. 7,014,669, 7,029,508 and 7,427,305 teach a composition for chemical mechanical polishing which comprises at least one abrasive particle having a surface at least partially coated by a catalyst. The catalyst comprises a metal other than a metal of Group 4(b), Group 5(b) or Group 6(b). The composition further comprises at least one oxidizing agent. The composition is believed to be effective by virtue of the interaction between the catalyst coated on the surface of the abrasive particles and the oxidizing agent, at the catalyst surface. The invention further provides a method that employs the composition in the polishing of a feature or layer, such as a metal film, on a substrate surface. The invention additionally provides a substrate produced this method.

Young-Jae Kang et al (J. Colloid & Inter. Sci. 2010, 349, 402-407) disclose a new method of Fe (metal) precipitation on colloidal silica to overcome the stability problem, which would be responsible in producing defects, with commercially available fumed silica slurry containing Fe ions. More specifically, Young-Jae Kang et al have synthesized colloidal silica particles using sodium silicate ($Na_2SiO_3$) as raw material with and without Fe precipitation by ion exchange process.

J. Colloid & Inter. Sci. 2005, 282, 11-19, studied the synthesis and characterization of iron oxide-coated silica. A three-level fractional factorial study was used to determine the optimum conditions for producing goethite-coated silica. The amount of coating achieved was between 0.59 and 21.36 mg Fe g–1 solid. The most significant factor in coating using either adsorption or precipitation was the particle size of silica, where Fe increased from an average of 0.85 to 9.6 mg Fe g–1 solid as silica size decreased from 1.5 to 0.2 mm. Other factors investigated, including coating temperature, initial iron concentration, and contact time, were of less importance. The iron oxide coatings were observed to be non-uniform, concentrated in rough concave areas. FTIR revealed a band shift as well as a new band indicating changes in the chemical environment of Fe—O and Si—O bonds; these results along with abrasion studies suggest that the interaction between the oxide coating and silica surface potentially involves chemical forces. Because the nano-sized iron oxide coatings increased surface area, introduced small pores, and changed the surface charge distribution of silica, the coated system demonstrates a greater affinity for Ni compared to that of uncoated silica.

US2013/0068995 discloses a silica having metal ions absorbed thereon and a fabricating method thereof are provided. The silica having metal ions absorbed thereon is a silica having metal ions absorbed thereon and being modified with persulfate salt. The method includes following steps. A solution is provided, and the solution includes silica and persulfate salt therein. The solution is heated to react the silica with the persulfate salt, so as to obtain silica modified with persulfate salt. Metal ion source is added in the solution, the metal ion source dissociates metal ions, and the silica modified with persulfate salt absorbs the metal ions to obtain the silica having metal ions absorbed thereon.

There is a significant need for tungsten CMP process(es) and slurry(s) that afford low dishing and plug recess effects especially in view of the fact that the semiconductor industry continues to move towards smaller and smaller feature sizes.

BRIEF SUMMARY OF THE INVENTION

Present invention discloses metal compound chemically anchored colloidal particles, which are colloidal particles having metal compounds uniformly anchored to surfaces of colloidal particles via chemical bonding. The metal compounds are in molecular form. The chemical bonding between the particle and the metal compound may be covalent, ionic, hydrogen bonding, or through Van der Waal forces. More preferably the bonding is covalent in nature. These metal compounds bonded to the particles may also be referred to as activator. The metal compound chemically anchored colloidal particles can be used as novel solid catalysts in CMP process. All the metal compounds are available for the catalysis reaction in CMP processes since the metal compounds are in molecular form.

In one aspect, the invention provides metal compound chemically anchored colloidal particles comprising:
  colloidal particles;
  metal compounds uniformly anchored on surfaces of the colloidal particles via chemical bonding;
  wherein the metal compounds are in molecular form.

In another aspect, the invention provides a method of making metal compound chemically anchored colloidal particles comprising:
  providing a solution comprising colloidal particles;
  providing a soluble metal compound precursor;
  providing an organic linking agent containing a functional group selected from the group consisting of amine, carboxylic acid, and combinations thereof;
  mixing the solution comprising colloidal particles, the organic linking agent and the soluble metal compound precursor; and
  forming the metal compound chemically anchored colloidal particles;
  wherein
  the organic linking agent modifies colloidal particle surfaces and anchors metal compounds uniformly onto the colloidal particle surfaces via chemical bonding to form the metal compound anchored colloidal particles; and
  the metal compound are in molecular form.

In yet another aspect, the invention provides a polishing composition comprising:
  0.01-1.00 wt % metal compound chemically anchored colloidal particles, wherein the metal compounds are uniformly anchored on surfaces of colloidal particles via chemical bonding and are in molecular form;
  0-10 wt % abrasive;
  0.05-10 wt % oxidizer; and
  liquid carrier;
  wherein
  pH of the composition is from about 2.0 to about 12.

In yet another aspect, the invention provides a method of chemical mechanical polishing a semiconductor substrate having at least one surface containing metal, comprising steps of:
  a) providing the semiconductor substrate;
  b) providing a polishing pad;
  c) providing a polishing composition comprising
    1) 0.01-1.00 wt % metal compounds chemically anchored colloidal particles, wherein the metal compounds are uniformly anchored on surfaces of colloidal particles via chemical bonding and are in molecular form;
    2) 0-10 wt % abrasive;
    3) 0.05-10 wt % oxidizer; and
    4) liquid carrier;
    wherein pH of the composition is from about 2.0 to about 12;

d) contacting the at least one surface containing metal with the polishing pad and the polishing composition; and e) polishing the at least one surface containing metal;
wherein
the metal is selected from the group consisting of tungsten (W), copper(Cu), Cobalt (Co), ruthenium (Ru), tantalum(Ta), and combinations thereof; and
at least a portion of the at least one surface containing metal is in contact with both the polishing pad and the polishing composition.

In yet another aspect, the invention provides a system for chemical mechanical planarization of a semiconductor substrate comprising at least one surface containing metal, the system comprising:

a polishing pad; and a polishing composition comprising
a) 0.01-1.00 wt % metal compounds chemically anchored colloidal particles wherein the metal compounds are uniformly anchored on surfaces of colloidal particles via chemical bonding and are in molecular form;
b) 0-10 wt % abrasive;
c) 0.05-10 wt % oxidizer; and
d) liquid carrier;
wherein pH of the composition is from about 2.0 to about 12;
wherein in use of the system the at least one surface containing metal is in contact with the polishing pad and the polishing composition.

The colloidal particles include, but are not limited to silica particles, lattice doped silica particles, germania particles, alumina particles, lattice doped alumina particles, titania particles, zirconium oxide particles, ceria particles, organic polymeric particles, and combinations thereof; the size of the colloidal particles is in the range of 5-1000 nm, preferably 10-500 nm, more preferably 15-250 nm.

Metal compounds may comprise compounds of metals of Group 1(b) or Group 8. The metal compound includes, but is not limited to compounds of Fe, Ru, Rh, Ir, Pt, Ag, Au, Cu, and Pd. Generally, the preferred activators are iron, copper, cerium, nickel, manganese, and/or cobalt. They can be used in any combination. The more preferred activators are iron or cerium salts.

The soluble metal compound precursor includes, but is not limited to a metal compound precursor containing carboxylic functional group, 1-amino-ω-(hydroxyamino)alkane chelating agent, or combinations thereof.

The soluble metal compound precursor containing carboxylic functional group includes, but is not limited to ammonium iron citrate, iron oxalates, iron acetates, iron tartrates, and iron complexes with various chelating agents selected form the group consisting of nitrilo acetic acid, ethylenediamine tetraacetic acid, phosphonic acids, phosphone acids, glycolic acid, lactic acid, malic acid, tartaric acid, or other α-hydroxy carboxylic acid-based agents or siderophores dihydroxyphenylalanine (DOPA); ω-N-hydroxy amino acids, and combinations thereof.

The organic linking agent includes, but is not limited to the agent having a general molecular structure selected from the group consisting of and combinations thereof;
wherein n, m, p, q refer to the numbers of (—CH$_2$—) groups between oxygen atoms connected to silicon atom and the methyl groups and range from 1 to 12.

Specific examples of the organic linking agents include, but are not limited to (3-Aminopropyl)triethoxysilane (APTES), octadecyl dimethyl ethoxysilane, (3-aminopropyl)-diethoxy-methylsilane, (3-aminopropyl)-dimethylethoxysilane, (3-aminopropyl)-trimethoxysilane, Ethyl(dimethyl)ethoxysilane, 3-(Carboethoxy)propyl dimethyl ethoxysilane, glycidoxypropyltrialkoxysilane, isocyanatopropyltrialkoxysilane, ureidopropyltrialkoxysilane, mercaptopropyltrialkoxysilane, cyanoethyltrialkoxysilane, 4,5-dihydro-1-(3-trialkoxysilylpropyl)imidazole, 3-(trialkoxysilyl)-methyl ester propenoic acid, trialkoxy[3-(oxiranylalkoxy)propyl]-silane, 2-methyl, 3-trialkoxysilyl) propyl ester 2-propenoic acid, [3-(trialkoxysilyl)propyl] urea, N-[(3-Trimethoxysilyl)propyl]ethylenediamine triacetic acid, trimethoxysilylpropyldiethylenetriamine and combinations hereof.

The abrasive particles includes, but is not limited to silica, alumina, titania, ceria, zirconia, diamond particles, silicon nitride particles, mono-modal, bi-modal, multi-modal colloidal particles, organic polymer-based soft abrasives, surface-coated or modified particles, and combinations thereof. Size of the abrasive particles as measured by any suitable technique such as dynamic light scattering, electron microscopy, disc centrifuge techniques is preferably between 0.001 to 1000 μm, or preferably between 0.01 to 10 μm, or most preferably between 0.03 to 0.1 μm.

The oxidizer includes, but is not limited to hydrogen peroxide and other per-oxy compounds, periodic acid, potassium iodate, potassium permanganate, ammonium persulfate, ammonium molybdate, ferric nitrate, nitric acid, potassium nitrate, and combinations thereof.

In another important embodiment, activator can react with a compound that produces free radicals. Activators can be held in a matrix such that the fluid containing the compounds that form free radicals contacts the activator immediately before contacting the substrate.

Preferably, the activator can function effectively without actinic radiation. In certain embodiments the actinic radiations may be used to enhance the reaction rates Optionally, the polishing composition further comprises one or more of the following:
a corrosion inhibitor;
a pH adjusting agent;
a surfactant; and
a biocide.

BRIEF DESCRIPTION OF SEVERAL VIEWS OF THE DRAWINGS

In the accompanying drawing forming a material part of this description, there is shown.

DETAILED DESCRIPTION OF THE INVENTION

Metal compound chemically anchored colloidal particles; a facile and fast process to chemically anchor metal compounds onto colloidal particles surfaces; a CMP slurry using metal compound chemically anchored colloidal particles; are disclosed in present invention.

Metal compounds are chemically linked to the surfaces of colloidal particles via an organic linking agent. Metal compounds remain in molecular form after the process. The invented process herein yields the uniform anchoring of metal compounds on the surfaces of colloidal particles.

When those metal compound chemically anchored colloidal particles are used in CMP slurry, all the metal compounds chemically anchored colloidal particles will be available for the catalysis reaction in a CMP process.

The colloidal particles include, but are limited to silica particles, lattice doped silica particles, germania particles, alumina particles, lattice doped alumina particles, titania particles, zirconium oxide particles, ceria particles, organic polymeric particles, and combinations thereof.

The organic polymeric particles include, but are not limited to carboxylic acid polymers such as those derived from monomers like acrylic acid, oligomeric acrylic acid, methacrylic acid, crotonic acid and vinyl acetic acid. Molecular weight of these polymers may be from 20000 to 10000000.

The colloidal particles can have various sizes. The size of colloidal particles ranges between 5-1000 nm, preferably 10-500 nm, most preferably 15-250 nm for CMP application. The colloidal particles can have various kinds of shapes, such as sphereical, cocoon, cubic, rectangular, aggregate, tec.

A colloidal particle solution contains 0.01 to 30 wt % of colloidal particles. The remaining is solvent, such as distilled water, and deionized (DI) water.

Metal compounds may comprise compounds of transition metals like copper, manganese, cobalt, and cerium, as well as the more traditional iron and copper. In one important embodiment, metal-containing compound is having the metal other than a metal of Group 4(b), Group 5(b) or Group 6(b) of the Periodic Table of Elements. In one embodiment, compounds of metals of Group 1(b) or Group 8 are preferred metal-containing compounds.

The metal compound includes, but is not limited to compounds of Fe, Ru, Rh, Ir, Pt, Ag, Au, Cu, and Pd. Generally, the preferred activators are iron, copper, cerium, nickel, manganese, and/or cobalt. They can be used in any combination. The more preferred activators are iron or cerium salts.

The metal compound precursor is water soluble. The water soluble metal compound precursor includes, but is not limited to a soluble metal compound precursor containing carboxylic functional group, 1-amino-ω-(hydroxyamino)alkane chelating agent, or combinations thereof.

The soluble metal compound precursor containing carboxylic functional group includes, but is not limited to ammonium iron citrate, iron oxalates, iron acetates, iron tartrates, and iron complexes with various chelating agents selected form the group consisting of nitrilo acetic acid, ethylenediamine tetraacetic acid, phosphonic acids, phosphone acids, glycolic acid, lactic acid, malic acid, tartaric acid, or other α-hydroxy carboxylic acid-based agents, siderophores dihydroxyphenylalanine (DOPA); ω-N-hydroxy amino acids, and combinations thereof.

An organic linking agent chemically modifies colloidal particle surfaces, and still maintains suitable functional groups on the surface of modified particles to further allow the anchoring of water soluble metal compounds onto the particle surfaces to obtain immobilized metal compounds. The metal compounds are chemically linked to the surface of colloidal particles. Metal compounds remain in molecular form after the process. Thus, the immobilized metal compounds are homogeneously distributed on the surfaces of colloidal particles. All those immobilized metal compounds are acting as solid state catalyst.

An organic linking agent includes but is not limited to organic silane compounds containing amine and/or carboxylic acid functional groups.

One of the suitable organic silane compounds containing amine has the general molecular structure as shown below:

Where n, m, p, q refer to the numbers of (—CH$_2$—) groups between oxygen atoms connected to silicon atom and the methyl groups, and between oxygen atom and amine group. These n, m, p, q numbers are ranged from 1 to 12 independently.

These methylene group numbers can have the following possible combinations:
1. While all the numbers are equal, n=m=p=q;
2. While with three numbers are same, but one number is different from other three numbers, such as n=m=p≠q; n=m=q≠p; n=p=q≠m; and m=p=q≠n.
3. Or more optionally, there are two methylene (—CH$_2$—) units that are the same, and other two methylene unit numbers are the same.
4. Or more optionally, all these four methylene group units can have all different numbers from each other, e.g. n≠m≠p≠q.

There are also other methylene group linkage unit length combinations that can be linked onto colloidal particle surfaces through chemical coupling reactions, which allow more wide range selections on the organic silane compounds.

Example includes but is not limited to (3-aminopropyl) triethoxysilane (APTES), octadecyl dimethyl ethoxysilane, (3-aminopropyl)-diethoxy-methylsilane, (3-aminopropyl)-dimethyl-ethoxysilane, (3-aminopropyl)-trimethoxysilane, Ethyl(dimethyl)ethoxysilane, 3-(carboethoxy)propyl dimethyl ethoxysilane.

Another type of organic silane containing carboxylic acid has the general molecular structure as shown below:

As indicated earlier, n, m, p, q numbers represent the numbers of methylene groups (—CH$_2$—) between oxygen atoms connected to silicon atom and the methyl groups and between oxygen atom and carboxylic acid group. These n, m, p, q numbers are ranged from 1 to 12 independently.

The combinations of these methylene group numbers have been described above.

Example includes but is not limited to glycidoxypropyltrialkoxysilane, isocyanatopropyltrialkoxysilane, ureidopropyltrialkoxysilane, mercaptopropyltrialkoxysilane, cyanoethyltrialkoxysilane, 4,5-dihydro-1-(3-trialkoxysilylpropyl)imidazole, 3-(trialkoxysilyl)-methyl ester propenoic acid, trialkoxy[3-(oxiranylalkoxy)propyl]-silane, 2-methyl, 3-trialkoxysilyl)propyl ester 2-propenoic acid, [3-(trialkoxysilyl)propyl]urea, N-[(3-Trimethoxysilyl)propyl]ethylenediamine triacetic acid, trimethoxysilylpropyldiethylenetriamine and combinations thereof.

Both amine and carboxylic acid functional groups can be linked onto colloidal particle surfaces through chemical coupling reactions. Amine and carboxylic acid functional groups on the chemical modified colloidal particle surfaces can then be used to directly anchor the homogeneous metal complex salt and convert them into the immobilized metal compounds which can be used as solid state catalyst.

The weight % ratio of the metal compound precursor to the colloidal particles ranges from 0.001 to 3; and molar ratio of the organic linking agent to the metal compound precursor is 0.001 to 10.

In one embodiment, various sized colloidal silica particles and iron compounds are used for the preparation of iron compound chemically anchored colloidal silica particles. The process of chemically anchoring metal compounds from a metal compound precursor onto colloidal particles surfaces is developed via an organic linking agent.

For instance, chemically anchoring iron compounds from ammonium iron citrate (iron compound precursor) onto colloidal silica particles surfaces is developed via 3-Aminopropyl)triethoxysilane (APTES) (an organic linking agent).

In this production process, APTES link to, and thus modify the colloidal silica particles through the coupling reactions of Si (silane in APTES) with O (oxygen on the surfaces of colloidal silica particles), APTES still maintain suitable functional amine groups on the surfaces of modified silica particles to further allow the reactions of anchoring water soluble iron compounds chemically onto the surfaces of colloidal silica particles to obtain the immobilized iron compounds.

Iron compounds remain in molecular form after the process. The process thus yield uniformly and chemically anchored iron compounds on the surfaces of colloidal silica particles. Please note that all irons will be available for the catalysis reaction in CMP process.

In the production process, colloidal (e.g. silica) particles, the organic linking agent (e.g. (3-Aminopropyl) triethoxysilane) (APTES) and the iron compound (e.g. ammonium iron citrate) can be mixed together under a temperature ranging from 16° C. to 100° C.

The mixing sequences can be in any orders/combinations. Such as, iron compound (e.g. ammonium iron citrate) can be mixed with organic linking agent (e.g. (3-Aminopropyl) triethoxysilane) (APTES) first. And then colloidal (e.g. silica) particles can be added to the mixture. Or, an organic linking agent (e.g. (3-Aminopropyl)triethoxysilane) (APTES) can be mixed with colloidal (e.g. silica) particles first. And then iron compound (e.g. ammonium iron citrate) can be added to the mixture.

Chemical structures of the starting and ending materials of the production process can be illustrated in scheme 1 as shown below.

Scheme 1. Chemical structures of starting materials and end materials.

The product or ending material of the process is iron compound chemically anchored colloidal silica particles.

In some embodiments the metal compounds chemically anchored to the particle surfaces may be used as heterogeneous catalysts in variety of applications such as but not limited to water phase oxidation, Fenton reaction catalysis, semiconductor photocatalysis, heterogeneous catalytic sonolysis, various hydrogenating processes, denitrification process, hydrodearomatization, hydrodesulfurization and organic synthesis reactions. Some of these applications have been described by Kari Pirkaanniemi and Mika Sillanpaa (Chemosphere 48 (2002) 1047-1060) and by Ingmar Bauer and Hans-Joachim Knolker (Chemical Reviews 115 (2015) 3170-3387).

In another embodiment, CMP polishing slurry (or composition) for polishing semiconductor substrate containing metals including but not being limited to tungsten (W), copper (Cu), Cobalt (Co), ruthenium (Ru), tantalum (Ta), and combinations thereof, using the metal compound chemically anchored colloidal particles as the solid catalyst can be prepared.

Anchoring or attaching metal compounds (such as iron catalyst) chemically to colloidal particles (such as silica particles) surface in molecular form is the most efficient way to utilize them as the catalyst in CMP slurry. Firstly, all metal atoms (active sites for catalytic reaction) are readily-accessible for solution species. Secondly, during polishing, chemical reaction is happing between oxidizer, metal substrate in the presence of catalyst. The closer of the catalyst to the metal substrate, the more efficient the catalyst is. For example, if metal exists in particle form, only the metal atoms on the surface of the particle are able to behave as catalytic sites. If metal molecule is not attached on the surface of colloidal particle, some or most of metal active sites are far away from the surface of the metal substrate during reaction and not contributing to the chemical reaction (hydroxyl radical formed has certain life time and will re-combine unless reaching and reacting with metal substrate). Thus, by attaching metal compound onto silica particle surface, much lower concentration of metal can be added into slurry while still achieving high metal RR, which will potentially translate to lower metal contamination after polishing.

Anchoring metal compound onto colloidal particle surfaces chemically also eliminates common problems when using soluble metal compound—stability over pH range. Metal compound normally is sensitive to pH and will lose the stability out of certain pH range. Anchoring soluble metal compound onto particle surface chemically overcomes this problem and give a much wider pH range with good stability.

The CMP polishing slurry or composition in the present invention comprises of metal compound chemically anchored on colloidal particles, nano-sized abrasive, oxidizer, corrosion inhibitor, and remaining is substantially liquid carrier.

The metal compound chemically anchored on colloidal particles described in present invention can be used as the solid state form of catalysts in CMP processes.

The CMP slurry contains metal compound chemically anchored on colloidal particles ranging 0.01 wt % to 10 wt %; preferably ranging from 0.1 wt % to 0.5 wt %.

Nano-sized abrasive particles used for the CMP polishing slurries include, but are not limited to, silica, alumina, titania, ceria, zirconia, nano-sized diamond particles, nano-sized silicon nitride particles, mono-modal, bi-modal, multi-modal colloidal abrasive particles, organic polymer-based soft abrasives, surface-coated or modified abrasives, and combinations thereof. Silica can be colloidal silica with narrow or broad particle size distributions, with various sizes and with various shapes, the various shapes of the abrasives include spherical shape, cocoon shape, aggregate shape and other shapes, the colloidal silica particles doped by other metal oxide within lattice of the colloidal silica, such as alumina doped silica particles. Alumina can be colloidal aluminum oxide, which include alpha-, beta-, and gamma-types of aluminum oxides. Titania can be colloidal and photoactive titanium dioxide. Ceria can be cerium oxide, or colloidal cerium oxide. Zirconia can be zirconium oxide.

The CMP polishing slurries contain 0.01 wt % to 30 wt % abrasives; preferably, the from 0.5 wt % to 5 wt %.

Oxidizers used for the disclosed tungsten CMP slurries include, but are not limited to, hydrogen peroxide and other per-oxy compounds, periodic acid, potassium iodate, potassium permanganate, ammonium persulfate, ammonium molybdate, ferric nitrate, nitric acid, potassium nitrate, and combinations thereof. The preferred oxidizer is hydrogen peroxide.

The CMP slurry of this invention contains 0.1 wt % to 10 wt % of an oxidizer; the preferably from 1 wt % to 4 wt %, and most preferably from 2 wt % to 3 wt %.

The corrosion inhibitor includes, but is not limited to: potassium cyanate, polyethylenimine, and other organic polymeric or oligomeric primary and secondary amines.

The CMP slurry contains corrosion inhibitors ranging from 0.0001 wt % to 2 wt %, preferably ranging 0.0001 wt % to 0.25 wt %; more preferably ranging from 0.0003 wt % to 0.01 wt %.

The liquid carrier which provides the principle portion of the liquid component can be water or mixtures of water with other liquids that are miscible with water. Advantageously the solvent is water, such as DI water.

The chemical mechanical polishing (CMP) slurry can further comprise one or more of the following:
a corrosion inhibitor
a pH adjusting agent;
a surfactant;
and
a biocide.

The corrosion inhibitor includes, but is not limited to potassium cyanate, polyethylenimine, other organic polymeric or oligomeric primary and secondary amines; and combinations thereof.

The CMP slurry of this invention contains 0.0001 wt % to 2 wt %; preferably 0.0001 wt % to 0.25wt %; corrosion inhibitor.

pH adjusting agents used for the CMP slurry include, but are not limited to, acids such as nitric acid, inorganic or organic acids, and combinations thereof; bases such as sodium hydroxide, potassium hydroxide, ammonium hydroxide, inorganic base or organic bases The preferred pH adjusting agent is nitric acid and potassium hydroxide.

The CMP slurry of this invention contains 0.01 wt % to 0.5 wt % pH adjusting agents; preferably from 0.05 wt % to 0.15 wt %.

The surfactants used for the disclosed tungsten CMP slurries include, but are not limited to the following
(a). Non-Ionic Surface Wetting Agents These agents typically are oxygen- or nitrogen-containing compounds with various hydrophobic and hydrophilic moieties in the same molecules, the molecular weight ranges from several hundreds to over 1 million. The viscosities of these materials also possess a very broad distribution.

(b). Anionic Surface Wetting Agents

These compounds possess the negative net charge on major part of molecular frame, these compound include, but not limited to the following salts with suitable hydrophobic tails, such as alkyl carboxylate, alkyl sulfate, alkyl phosphate, alkyl bicarboxylate, alkyl bisulfate, alkyl biphosphate, such as alkoxy carboxylate, alkoxy sulfate, alkoxy phosphate, alkoxy bicarboxylate, alkoxy bisulfate, alkoxy biphosphate, such as substituted aryl carboxylate, substituted aryl sulfate, substituted aryl phosphate, substituted aryl bicarboxylate, substituted aryl bisulfate, substituted aryl biphosphate etc. The counter ions for this type of surface wetting agents include, but not limited to the following ions, such as potassium, ammonium and other positive ions. The molecular weights of these anionic surface wetting agents range from several hundred to several hundred-thousands.

(c). Cationic Surface Wetting Agents

These cationic surface wetting agents possess the positive charge on major frame part of the molecular frame. The cationic surfactants include, but are not limited to benzalkonium chloride, benzethonium chloride, bronidox, cetrimonium bromide, cetrimonium chloride, distearyldimethylammonium chloride, lauryl methyl gluceth-10 hydroxypropyl diammonium chloride, olaflur, tetraalkyl ammonium chloride, tetraalkylammonium hydroxide, and combinations thereof.

(d). Ampholytic Surface Wetting Agents

These compounds possess both of positive and negative charges on the main molecular chains and with their relative counter ions. The examples of such bipolar surface wetting agents include, but not limited to the salts of amino-carboxylic acids, amino-phosphoric acid, and amino-sulfonic acid.

The surfactants used in the tungsten CMP slurries range from 0.0001% to 0.50%; preferably range from 0.0005% to 0.10%.

The biocides used for the disclosed tungsten CMP slurries include, but are not limited to those commercial available biocide products, such as Kathon, Kathon II and others.

The biocides used in the tungsten CMP slurries ranging from 0.0001% to 0.1%; preferably ranging from 0.0005% to 0.010.

For a CMP slurry, removable rate (RR) (Å/min.) and Within Wafer non-uniformity % (WIWNU %) are used to measure the performance of the slurry. An increased RR and reduced WIWNU % are indications of better performance of a slurry.

Removal Rate (RR) is the average amount of material removed in a given time, typically calculated over a great number of points:

$$RR = \frac{\Sigma \text{ (Pre-polish thickness-Post-polish thickness)/\# of points}}{\text{Time of polishing}}$$

In addition, the removal rate on polishing dielectric films is not affected while the tungsten film removal rate is boosted. Thus, the selectivity of polishing tungsten/dielectric (W/D) films can be increased to afford tungsten CMP polishing slurries with higher selectivity of polishing W/D films.

The present invention is further demonstrated by the examples below.

WORKING EXAMPLE

The associated methods described herein entail use of the aforementioned slurry for chemical mechanical planarization of substrates comprised of tungsten.

In production process, iron compound chemically anchored colloidal silica particles are synthesized.

In CMP processes, the polishing slurry and associated methods described herein are effective for CMP of a wide variety of substrates, including most of substrates having surfaces containing metal selected from the group consisting of tungsten (W), copper (Cu), Cobalt (Co), ruthenium (Ru), tantalum (Ta), and combinations thereof.

In the working examples, a substrate containing tungsten (e.g., a wafer with W surface) is placed face-down on a polishing pad which is fixedly attached to a rotatable platen of a CMP polisher. In this manner, the substrate to be polished and planarized is placed in direct contact with the polishing pad. A wafer carrier system or polishing head is used to hold the substrate in place and to apply a downward pressure against the backside of the substrate during CMP processing while the platen and the substrate are rotated. The polishing slurry (composition) is applied (usually continuously) on the pad during CMP processing to effect the removal of material to planarize the substrate.

General Experimental Procedure

In the examples presented below, CMP experiments were run using the procedures and experimental conditions given below.

The CMP tool that was used in the examples is a Mirra®, manufactured by Applied Materials, 3050 Boweres Avenue, Santa Clara, Calif., 95054. An IC-1010 pad, supplied by Dow Chemicals, was used on the platen for the blanket wafer polishing studies. Pads were broken-in by polishing twenty-five dummy oxide (deposited by plasma enhanced CVD from a TEOS precursor, PETEOS) wafers.

In order to qualify the tool settings and the pad break-in, two PETEOS monitors were polished with Syton® OX-K colloidal silica, supplied by Planarization Platform of Air Products Chemicals Inc. at baseline conditions. Polishing experiments were conducted using blanket W wafer with 8K Angstroms in thickness, and TEOS wafer. These blanket wafers were purchased from Silicon Valley Microelectronics, 1150 Campbell Ave, CA, 95126

Parameters

Å: angstrom(s)—a unit of length
W: tungsten
BP: back pressure, in psi units
CMP: chemical mechanical planarization=chemical mechanical polishing
CS: carrier speed
DF: Down force: pressure applied during CMP, unit psi
min: minute(s)
ml: milliliter(s)
mV: millivolt(s)
psi: pounds per square inch
PS: platen rotational speed of polishing tool, in rpm (revolution(s) per minute)
SF: polishing composition flow, ml/min
wt %: weight percentage (of a listed component)
TEOS: tetraethylorthosilicate
NU % (or WIWNU %): With-In Wafer Non-Uniformity %

NU %=(|W film thickness pre-polishing−W film thickness post-polishing|/mean of total W film thickness)×100%

W RR 3.0 psi: Measured tungsten removal rate at 3.0 psi down pressure of the CMP tool
TEOS RR 3.0 psi: Measured TEOS removal rate at 3.0 psi down pressure of the CMP tool
W:TEOS Selectivity: (removal rate of W)/(removal rate of TEOS) at same down force (3.0 psi)

Iron Compound Chemically Anchored Colloidal Silica Particles 1000 ppm APTES was added to 500 g solution contained 3 wt % silica solution. The silica particles were ~30 nm in diameter. pH of the solution was adjusted to below 4 by adding $HNO_3$. The solution was heated at 80° C. for 2 hours.

600 ppm ammonium iron citrate (~100 ppm Fe) was added to the heated solution. The result solution was heated for another 2 hours.

Alternately, APTES and ammonium iron citrate were mixed first in the solution. The solution was heated at 80° C. for 2 hours. Then silica solution was added to the solution and continued heating for another 2 hours. All chemical constitutes in the final solution were kept the same as the first process: 3 wt % silica, 1000 ppm APTES and 600 ppm ammonium iron citrate.

Iron compound chemically anchored colloidal silica particles were obtained.

Figure 1:
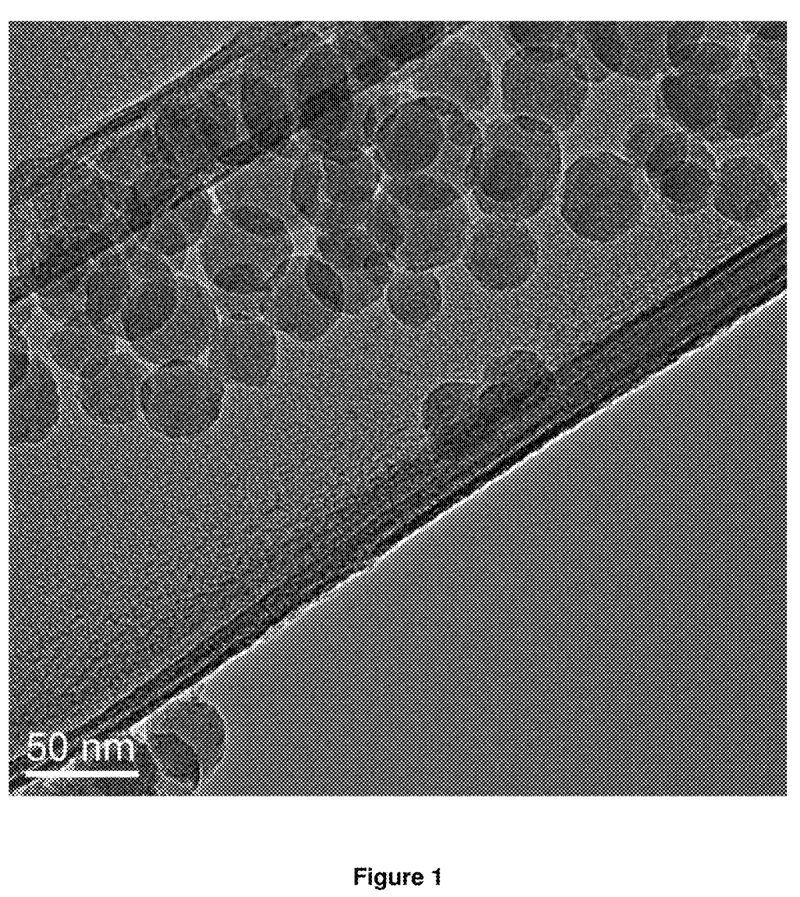
FIG. 1 depicts the transmission electron microscopy (TEM) images of the prepared silica particles having iron compound chemically anchored on the surfaces.

FIG. 1 showed Transmission Electron Microscopy (TEM) images of the prepared iron compound chemically anchored colloidal silica particles. The iron compounds are anchored onto colloidal silica particles via chemical bonding.

Figure 2:
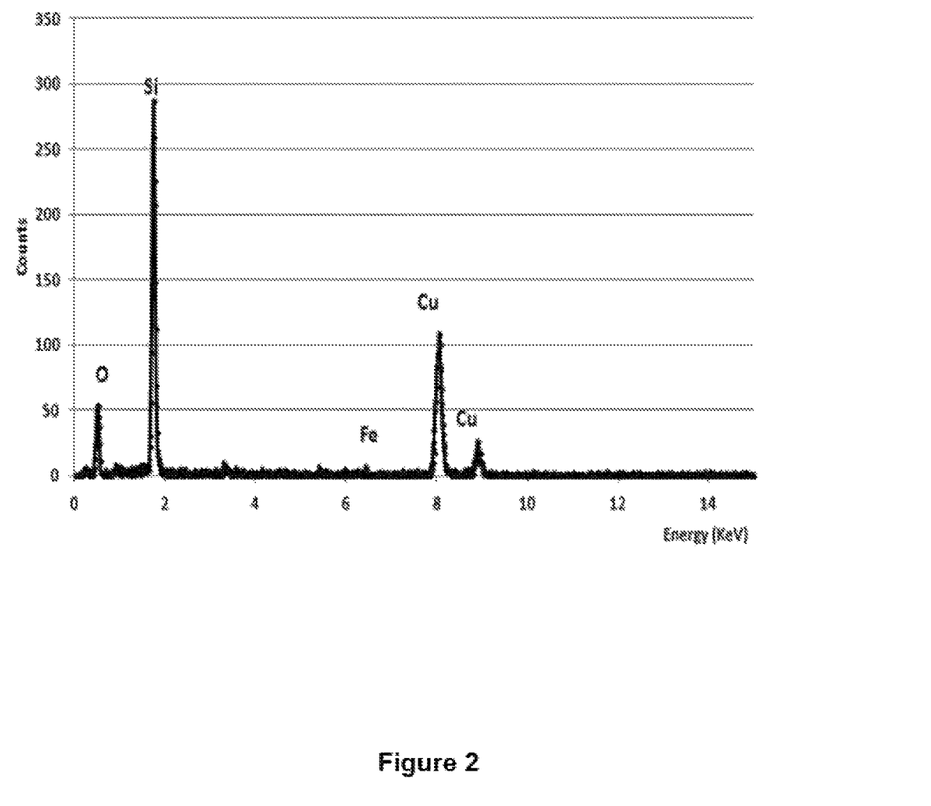
FIG. 2 depicts the energy dispersive spectra (EDS) of the prepared silica particles having iron compound chemically anchored on the surfaces.

FIG. 2 showed Energy Dispersive Spectra (EDS) of the prepared iron compound chemically anchored colloidal silica particles.

At the first look, it seemed that only silica particles were showed in the TEM image. Iron could not be seen from the TEM image. However, low signal of Fe peak in EDS confirmed the existence of iron. As discussed and illustrated in Scheme 1, iron compounds are anchored chemically to the surface of silica particle in the form of molecular instead of particles. Thus, TEM results agreed well with the discussed chemical structure. Iron compounds could not be seen in the TEM image because of their molecular form. Please note that the copper peak came from the TEM grid.

Soluble Iron Test

Soluble iron test was conducted to see if there was any soluble iron left in the solution. The procedure was carried out as described below.

The solution was centrifuged at 13,500 RPM for 1 hour. The supernatant was taken out. Full digestion of supernant (by mixture of $H_2O_2$ and sulfuric acid) was conducted by Inductively Coupled Plasma Atomic Emission Spectroscopy-(ICP-AES) to measure the iron level. The iron level was determined less than 1 ppm. Therefore, the results confirmed that near 100% iron was attached to the particles.

Control Experiments

To verify the function of each components in the synthesis or production process, three control experiments were performed. The results were summarized in Table 1 below.

The results from Experiments 1 and 3 indicated that APTES served as the chemical linking agent, as discussed and illustrated in Scheme 1. APTES reacted quickly with silica oxide particle (i.e. colloidal silica particles) surface and formed Si—O—Si bond. In this way, silica oxide particle surface now beard the functional group from APTES—amine group, which readily reacted with carboxylic acid group from the iron precursor—ammonium iron citrate and chemically anchored water soluble iron compounds onto the silica oxide particle surfaces to obtain the immobilized homogeneously distributed iron compounds.

TABLE 1

Experiments with different starting conditions.

| Exp. | particles | Iron precursor | Linking agent | results |
|---|---|---|---|---|
| 1 | Silica | Ammonium iron Citrate | APTES | Iron compound attaches to the silica |
| 2 | Silica | Ammonium iron sulfate | APTES | Most of the iron compound remains in the solution. |
| 3 | Silica | Ammonium iron Citrate | N/A | Most of the iron compound remains in the solution. |
| 4 | N/A | Ammonium iron Citrate | APTES | Solution remains the same yellow color and no particle formed. |

The results from Experiments 1 and 2 indicated that no attachment of iron compound would happen if the iron precursor (ammonium iron sulfate) has no carboxylic acid group (e.g. sulfate group). Thus, the iron precursor containing carboxylic acid group is vital to couple the iron precursor with the amine group on the surfaces of the colloidal silica particles, and thus anchor the iron compounds chemically to the surfaces.

Chemical Mechanical Polishing

Chemical Mechanical Polishing W substrate was carried out. Iron compound chemically anchored colloidal silica particles were used as solid catalyst. Three different CMP slurries were formed and used to polishing substrates containing W.

Standard CMP slurry without solid catalyst comprised
0.2 wt % colloidal silica having particles size of 160 nm;
3 wt % hydrogen peroxide;
0.27 wt % colloidal silica which was used as base particle for solid catalyst; and
the remaining is DI Water;
pH of the slurry is in the range of 7.0 to 8.0.
CMP slurry with solid catalyst made by the process of present invention comprised:
0.27 wt % solid catalyst-iron compound chemically anchored colloidal silica particles;
0.2 wt % colloidal silica having particles size of 160 nm;
3 wt % hydrogen peroxide; and
the remaining is DI Water;
wherein the colloidal silica particle has a diameter of 50 nm and pH of the slurry is in the range of 7.0 to 8.0.

The performances of CMP slurries with and without Iron compound chemically anchored colloidal silica particles (solid state catalysts) were measured and compared as shown in Table 2.

TABLE 2

Comparison of polishing performance

| Sample | W RR (Å/min) |
| --- | --- |
| CMP slurry (with solid catalyst made by process of present invention) | 6508 |
| Standard CMP slurry (without solid catalyst) | 2770 |

The results in Table 2 showed that CMP slurry containing the new solid catalyst made by the process disclosed in present invention gave a much higher W RR (2.35 times) compared to the standard CMP slurry without solid catalyst.

The CMP slurry containing the new solid catalyst had TEOS RR at 220 Å/min. Thus, the CMP slurry also offered high selectivity for removal of W vs TEOS.

Most importantly, CMP slurry containing the new solid catalyst gave a much lower Fe level (~11 ppm), thus much less metal contamination on the wafer after CMP.

The results indicated that Iron compound chemically anchored colloidal silica particles had uniform coating and higher loading of iron compound on the base colloidal particles as solid state catalyst. Every iron atom could be a catalysis center when they are anchored chemically to the colloidal particles surfaces chemically.

Using iron compound chemically anchored colloidal silica particles in CMP slurry resulted in better performances, that is, high metal RR (Å/min) while maintaining high selectivity for removal of metal vs dielectric material, and less metal contamination on the wafer after CMP.

The embodiments of this invention listed above, including the working example, are exemplary of numerous embodiments that may be made of this invention. It is contemplated that numerous other configurations of the process may be used, and the materials used in the process may be elected from numerous materials other than those specifically disclosed.

The invention claimed is:

1. Metal compound chemically anchored colloidal particles comprising:
   colloidal particles;
   metal compounds uniformly anchored on surfaces of the colloidal particles via an organic linking agent with chemical bonding;
   wherein
   the metal compounds are in molecular form;
   the colloidal particles are selected from silica particles, lattice doped silica particles, germania particles, alumina particles, lattice doped alumina particles, titania particles, zirconium oxide particles, ceria particles, organic polymeric particles, and combinations thereof; and size of the colloidal particles is in the range of 5-1000 nm; and
   the metal compounds are selected from Fe compounds, Cu compounds, Ag compounds, Cr compounds, Mn compounds, Co compounds, Ni compounds, Ga compounds, and combinations thereof.

2. The metal compound chemically anchored colloidal particles of claim 1, wherein the colloidal particles are silica particles; the metal compounds are iron compounds; and the metal compound chemically anchored colloidal particles are iron compound chemically anchored silica particles.

3. The metal compound chemically anchored colloidal particles of claim 2, wherein the iron compound is derived from a water soluble metal compound precursor selected from the group consisting of ammonium iron citrate; iron oxalate; iron acetate; iron tartrate; iron compound having chelating agent selected form the group consisting of nitriloacetic acid, ethylenediamine tetraacetic acid, phosphonic acid, phosphone acid, glycolic acid, lactic acid, malic acid, tartaric acid, α-hydroxy carboxylic acid, siderophores dihydroxyphenylalanine (DOPA), ω-N-hydroxy amino acid, and combinations thereof.

4. The metal compound chemically anchored colloidal particles of claim 1, wherein the metal compound is derived from a water soluble metal compound precursor containing a carboxylic functional group, 1-amino-ω-(hydroxyamino) alkane chelating agent, or combinations thereof.

5. The metal compound chemically anchored colloidal particles of claim 1, wherein the organic linking agent has a general molecular structure selected from the group consisting of (a)

-continued (b)

and combinations thereof;
wherein n, m, p, q are the numbers of methylene (—CH$_2$—) groups, and each is independently selected from a number from 1 to 12.

6. metal compound chemically anchored colloidal particles of claim 5, wherein the organic linking agent is selected from the group consisting of (3-Aminopropyl) triethoxysilane (APTES), octadecyl dimethyl ethoxysilane, (3-aminopropyl)-diethoxy-methylsilane, (3-aminopropyl)-dimethyl-ethoxysilane, (3-aminopropyl)-trimethoxysilane, Ethyl(dimethyl)ethoxysilane, 3-(Carboethoxy)propyl dimethyl ethoxysilane , glycidoxypropyltrialkoxysilane, isocyanatopropyltrialkoxysilane, ureidopropyltrialkoxysilane, mercaptopropyltrialkoxysilane, cyanoethyltrialkoxysilane, 4,5-dihydro-1-(3-trialkoxysilylpropyl)imidazole, 3-(trialkoxysilyl)-methyl ester propenoic acid, trialkoxy[3-(oxiranylalkoxy)propyl]-silane, 2-methyl, 3-trialkoxysilyl)propyl ester 2-propenoic acid, [3-(trialkoxysilyl)propyl]urea, N-[(3-Trimethoxysilyl)propyl]ethylenediamine triacetic acid, trimethoxysilylpropyldiethylenetriamine and combinations thereof.

* * * * *